US005792476A

United States Patent [19]
Hällgren

[11] Patent Number: 5,792,476
[45] Date of Patent: Aug. 11, 1998

[54] SUSTAINED RELEASE GLUCOCORTICOID PHARMACEUTICAL COMPOSITION

[75] Inventor: Roger Hällgren, Bälinge, Sweden

[73] Assignee: Abigo Medical AB, Askim, Sweden

[21] Appl. No.: 769,783

[22] Filed: Dec. 19, 1996

[51] Int. Cl.⁶ .................................................. A61K 9/20
[52] U.S. Cl. ............................................ 424/465; 424/489
[58] Field of Search ................................ 424/489, 468, 424/435, 465

[56] References Cited

U.S. PATENT DOCUMENTS

| | | | |
|---|---|---|---|
| 5,019,562 | 5/1991 | Folkman et al. | 514/58 |
| 5,128,320 | 7/1992 | Hahn et al. | 514/12 |
| 5,449,515 | 9/1995 | Hamilton et al. | 424/85.2 |

FOREIGN PATENT DOCUMENTS

| | | |
|---|---|---|
| 8007639-1 | 7/1986 | Sweden. |
| 87/00295 | 1/1988 | WIPO. |
| 90/00738 | 5/1991 | WIPO. |
| 91/00688 | 10/1991 | WIPO. |
| 94/02531 | 3/1995 | WIPO. |

OTHER PUBLICATIONS

"Time of Day Medicine Dose is Taken May Boost its Efficacy, Cut Toxicity," *Medical News & Perspectives, JAMA*, Apr. 17, 1996, vol. 275, No. 15, pp. 1143–1144.
Abstract of EP-656204.
Abstract of AU 9463426.
Abstract of JP 06256166.
Abstract of US 5,288,503.
Abstract of WO 9621448.
Abstract of US 5,536,507.
Abstract of WO 9611674.
Abstract of WO 9610397.
Abstract WO 9528916.
Abstract of US 5,541,171.
Abstract of JP 06-336444.
Abstract of US 5,160,744.
Abstract of EP 605174.
Abstract of US 5,178,867.
Abstract of US 5,102,668.
Abstract of US 4,863,742.
Abstract of EP 250267.
Abstract of EP 366868.

*Primary Examiner*—Thurman K. Page
*Assistant Examiner*—William E. Benston, Jr.
*Attorney, Agent, or Firm*—Beveridge, DeGrandi, Weilacher & Young LLP

[57] ABSTRACT

A pharmaceutical composition for peroral treatment of rheumatoid arthritis and a treatment method therefor are described, wherein said composition comprises 2.5–7 mg of a glucocorticoid as active substance with a regulated sustained release such that at least 90% by weight of the glucocorticoid is released during a period of about 40–80 min. starting about 1–3 h after the entry of said glucocorticoid into the small intestine of a mammal.

18 Claims, No Drawings

SUSTAINED RELEASE GLUCOCORTICOID PHARMACEUTICAL COMPOSITION

The present invention relates to a pharmaceutical composition for peroral treatment of rheumatoid arthritis.

BACKGROUND OF THE INVENTION

Since 1948, glucocorticoids have been used for treatment of rheumatoid arthritis. Glucocorticoids have a very favourable effect on the symptoms of rheumatoid arthritis, e.g. morning stiffness, joint pain and joint swelling. Since the late 40's peroral administration of glucocorticoids has taken place when the patient is awake, often during the early morning hours, i.e. not during the night. This treatment strategy has reduced the symptoms. During the treatment, however, a relatively high amount of glucocorticoid is used per dose, which leads to an increased risk for dose dependent adverse side effects, inter alia bone decalcification. The high dose used is actually too close to the doses leading to adverse effects, i.e. is close to toxical levels.

Therefore, it has been a long-felt need to reduce the dose level in view of eliminating the risk for the above-mentioned adverse side effects.

DESCRIPTION OF THE PRIOR ART

WO 95/08323 (Dr. Falk Pharma GmbH) describes a drug formulation with controlled release containing budesonide, a corticosteroid, as the active substance.

WO 91/07172 (Draco AB) describes an oral composition with controlled release for the treatment of inflammatory bowel diseases and use of certain glucocorticosteroids in the preparation of a pharmaceutical composition for oral treatment of ulcerative colitis and certain aspects of Crohn's disease.

WO 91/16042 (Eurand International Spa) describes a targeted drug formulation with controlled release for delivery of drugs to the small intestine and the colon of a mammal.

WO 88/00046 (Schering) describes controlled delayed release drug formulations, inter alia comprising prednisolone, a glucocorticoid, as the active substance.

The Swedish patent publication 445 886 refers to tablets for release of the active substance in the colon.

In JAMA, Apr. 17, 1996, vol 275, No. 15, in an article entitled Medical News and Perspectives (Lynne Lamberg), circadian rhythms and optimized administration of drug formulations are described, as well as treatment of rheumatoid arthritis with non-steroidal anti-inflammatory drugs.

EP-A1-656 204 describes circadian rhythms and a controlled released pharmaceutical tablet for treatment of diseases.

Further, AU-A-9 463 426 describes a pharmaceutical tablet capable of releasing drug(s) at subsequent times for therapeutic or protective treatment of disorders connected with circadian rhythms.

OBJECT OF THE INVENTION

The object of the present invention is to eliminate the above-mentioned problems in treatment of rheumatoid arthritis and thereby alleviate the symptoms and reduce the intensity thereof.

This object is achieved by a pharmaceutical composition of the type described by way of introduction and which is further characterised in that it comprises 2.5–7 mg of a glucocorticoid as active substance with a regulated sustained release such that at least 90% by weight of the glucocorticoid is released during a period of about 40–80 min, starting about 1–3 h after the entry of said glucocorticoid into the small intestine of a mammal.

Another aspect the present invention relates to a method for the treatment of rheumatoid arthritis by administrating a pharmaceutical composition according to the present invention to a patient before normal bed time in view of releasing the glucocorticoid into the small intestine at about 02.00–03.00 a.m.

The pharmaceutical composition according to the present invention has, to our knowledge, never been described in the state of the art.

SUMMARY OF THE INVENTION

Several diseases, such as asthma, osteoarthritis, cerebral hemorrhage, allergic rhinitis, and rheumatoid arthritis, follow the circadian rhythms, i.e. the biological rhythms of the body. Thus, the intensity peak time for these diseases has been studied and is now highly predictable.

Therefore, drug formulations for the treatment of these diseases should be designed to be synchronized with the circadian rhythms. The peak time for rheumatoid arthritis is e.g. about 06.00 a.m., i.e. shortly before normal wake-up time for most people.

The inventor has now surprisingly found that the amount of active substance, i.e. glucocorticoid, can be dramatically reduced by optimizing the pharmaceutical composition for the treatment of rheumatoid arthritis in such a way that almost all of the active substance is resorbed about 02.00–03.00 a.m. during the patient's sleep.

During a sustained release test according to US Pharmacopea Standards (USP XXI, apparatus No. 2, 100 rpm) in artificial gastric juice having a pH of 1.2, at most 10% by weight of a corticoid was released during 1 h, and at least 80% by weight of the corticoid was released during 3 h in a phosphate buffer having a pH of 6.8.

Corticoids, also called corticosteroids, are divided into mineral corticoids and glucocorticoids. The latter are used to a large extent for the treatment of several diseases. Their anti-inflammatory characteristics have made them useful for the treatment of e.g. rheumatoid arthritis. Examples of glucocorticoids are prednisolone, prednisolone, cortisone, betametasone, and triamcinolone.

In the case of rheumatoid arthritis, the pharmaceutical composition according to the present invention is preferably administered perorally before normal bed time for human beings, as it would be uncomfortable to be awakened during the best sleeping hours in the middle of the night to receive the drug formulation. This means that the active ingredient, i.e. the glucocorticoid, should be released several hours after the administration and during a specified short time in the middle of the night, preferably between about 02.00 and 03.00 a.m. Preferable active substances in the pharmaceutical composition for the treatment of rheumatoid arthritis are prenisolone or prenisolone, since these substances are very quickly resorbed in the small intestine and normally have a plasma peak concentration within about 1–3 hours after administration and a plasma half life of about 2–3.5 hours.

In the preferred embodiment of the present invention a core containing prednisolone in an amount of 5 mg is coated with a layer of 8% by weight of hydroxypropylmethylcellulosaphtalate (HP55), based on the total weight of the composition. The regulated sustained release takes place about 1–3 hours, preferably about 2 hours, after the passage of the pharmaceutical composition from the stomach to the small intestine. This means that the pharmaceutical composition should resist release during the passage of the stomach, i.e. during about 2 hours in gastric juice, having a HCl concentration of about 0.1N. Further, the pharmaceutical composition should resist another 2 hours, approximately, in the small intestine, i.e. in a medium corresponding to a phosphate buffer with a pH of 6.8. After the latter 2 hours, at least 80% by weight, preferably at least 90% by weight, of the active substance should be released during 40–80 min, preferably 60 min. This sustained release profile is optimal for the treatment of rheumatoid arthritis, and the on-set time for the active substance should take place about 3–4 hours before the peak time, which is at about 06.00 a.m., and about 4–5 hours before awakening, i.e. normally at about 02.00 to 03.00 a.m., to conform with the circadian rhythm for rheumatoid arthritis.

The low dose level of the active substance, i.e. 2.5–7 mg, preferably about 4–6 mg, and in the most preferable embodiment about 5 mg, is to be construed as a maintenance dose and is about 30–75% lower than the maintenance dose level of active substance conventionally used in drug formulations for treatment of rheumatoid arthritis. The conventional maintenance dose level of the active substance used in the present invention is 10–30 mg per day. In severe cases, the dose level may be increased to up to 50–60 mg per day, and is administered during some days. To make these low dose levels of active substance possible, the active substance is micronised, followed by wet granulation to form a granulate. Such a granulate has, as such; a release rate of 70% during 30 min in water of 37° C. Further, the granulate is laminated with a sustained release inner layer resistant to a pH of 6.8 and a sustained release outer layer resistant to a pH of 1.0. The inner layer is preferably made of Eudragit®RL (copolymer of acrylic and methacrylic esters with a low content of quaternary ammonium groups) and the outer layer is preferably made of Eudragit®L (anionic polymer synthesized from methacrylic acid and methacrylic acid methyl ester).

The active substance, i.e. the glucocorticoid, such as prednisolone or prednisone, is suitably mixed with known diluents, such as starch and lactose, and is preferably granulated with PVP (polyvinylpyrrolidone). During preparation of tablets, a glidant, such as talc and/or magnesium stearate, may also be added.

The present invention will now be further described in the following Example.

EXAMPLE

The treatment effect of peroral administration of glucocorticoids to 26 patients with rheumatoid arthritis was studied. Six of the patients were males at the ages of 54 to 80 years, the average age being 69 years, and 20 of the patients were women at the ages of 23 to 90 years, the average age being 62 years. The patients were randomly divided into two groups A and B. Group A received prednisolone as glucocorticoid at 02.00 a.m. and group B received prednisolone at 07.30 a.m. Both groups consisted of 13 patients each. In each group 4 patients received 7.5 mg prednisolone and 9 patients received 5 mg prednisolone. All of the patients received 4 doses of prednisolone altogether during 4 days and nights. Prior to the experiment and after the completed treatment period, each patient was clinically examined regarding the duration of morning stiffness, the degree of joint pain according to a 10 grade scale, and joint index, so called Lansbury's index, which evaluates the degree of joint arthritis. It turned out that the group of patients that received prednisolone during the night had, in average, a 5-fold improvement of the morning stiffness, a 3-fold improvement of pain during rest and a 4-fold improvement of joint index. The effects were statistically significant. In the group of patients that received prednisolone during the morning, no effect on pain during rest or joint index was observed, but a minor improvement of about 20% was observed for the morning stiffness. The effect differences between the both patient groups were statistically significant for the different variables.

Thus, this experiment shows that the same dose of a glucocorticoid preparation gives dramatically different effects on the joint symptoms of rheumatoid arthritis when administrated at different moments during the day and night. The result shows that the amount of glucocorticoid administrated can be reduced with up to about 50–75% if administrated during the night, or if absorbed during the night, compared to conventional early morning dosing.

In the table below, the results obtained are shown, inter alia clinical and laboratory data for the 26 patients with rheumatoid arthritis at day 1 and after 4 doses of prednisolone (day 5).

|  | Day 1 | | Day 5 | |
| --- | --- | --- | --- | --- |
|  | 02.00 a.m. (n = 13) | 07.30 a.m. (n = 13) | 02.00 a.m. (n = 13) | 07.30 a.m. (n = 13) |
| Age | 62 ± 4 | 64 ± 5 | | |
| Disease period | 10 ± 3 | 12 ± 4 | | |
| Morning stiffness | 242 ± 38 | 307 ± 103 | 53 ± 27** | 260 ± 104 |
| Pain during rest | 4.0 ± 0.7 | 3.5 ± 0.6 | 1.5 ± 0.4* | 3.4 ± 0.7 |
| Lansbury index | 130 ± 23 | 101 ± 19 | 33 ± 7** | 87 ± 13 |
| Ritchie index | 21 ± 3 | 16 ± 2 | 11 ± 2 | 14 ± 2 |
| ESR (mm/h) | 47 ± 9 | 41 ± 5 | 36 ± 5 | 31 ± 4 |
| Haptoglobin (g/l) | 2.8 ± 0.3 | 2.3 ± 0.3 | 2.7 ± 0.3 | 2.3 ± 0.3 |
| Hemoglobin | 115 ± 5 | 123 ± 3 | 118 ± 5 | 123 ± 3 |
| WBCx109 | 7.0 ± 0.4 | 7.0 ± 0.6 | 7.2 ± 0.4 | 7.4 ± 0.5 |
| RBCx109 | 308 ± 18* | 256 ± 14 | 336 ± 24 | 276 ± 15 |

ESR = erythrocyte sedimentation rate
WBC = leukocytes
RBC = red blood cells
* = p < 0.05
** = p < 0.01 with Mann-Whitney's U test

I claim:

1. A sustained release pharmaceutical composition for peroral treatment of rheumatoid arthritis, consisting essentially of:

2.5–7 mg of a glucocorticoid, and means for releasing at least 80% by weight of the glucocorticoid into the small intestine of a mammal during a period of about 40–80 min, starting about 1–3 h after the entry of the composition into the small intestine of said mammal.

2. The pharmaceutical composition of claim 1 wherein the glucocorticoid is selected from the group consisting of prednisolone and prednisone.

3. The pharmaceutical composition of claim 1 wherein the composition comprises 4–6 mg glucocorticoid.

4. The pharmaceutical composition of claim 1 wherein the composition comprises about 5 mg glucocorticoid.

5. A sustained release pharmaceutical composition for peroral treatment of rheumatoid arthritis, consisting essentially of:

2.5–7 mg of a glucocorticoid, said glucocorticoid being in a form such that at least 80% by weight of the glucocorticoid is released into the small intestine of a mammal during a period of about 40–80 min. starting about 1–3 h after the entry of the composition into the small intestine of said mammal.

6. The pharmaceutical composition of claim 5 wherein the glucocorticoid is selected from the group consisting of prednisolone and prednisone.

7. The pharmaceutical composition of claim 5 wherein said glucocorticoid being in a form such that at least 90% by weight of the glucocorticoid is released into the small intestine of a mammal during a period of about 40–80 min. starting about 1–3 h after the entry of the composition into the small intestine of said mammal.

8. A sustained release pharmaceutical composition for peroral treatment of rheumatoid arthritis. consisting essentially of:

a granulate core comprising 2.5–7 mg of a micronized glucocorticoid wherein said glucocorticoid is wet granulated with a polyvinylpyrrolidone, an inner layer covering said core wherein said inner layer is resistant to a pH of about 6.8, and an outer layer covering said inner layer wherein said outer layer is resistant to a pH of about 1.

9. The pharmaceutical composition of claim 8 wherein the glucocorticoid is selected from the group consisting of prednisolone and prednisone.

10. The composition of claim 9, wherein said consists essentially of:

a diluent selected from the group consisting of starch, lactose, and combinations thereof, and a glidant selected from the group consisting of talc, magnesium sterate, and combinations thereof.

11. The composition of claim 9, wherein said inner layer comprises a copolymer of an acrylic and a methacrylic ester with a low content of quaternary ammonium groups and said outer layer comprises an anionic polymer synthesized from a methacrylic acid and a methacrylic acid methyl ester.

12. A method for the treatment of rheumatoid arthritis comprising:

perorally administering to a patient in need thereof, a sustained release pharmaceutical composition for treatment of rheumatoid arthritis, consisting essentially of:

2.5–7 mg of a glucocorticoid, and means for releasing at least 80% by weight of the glucocorticoid into the small intestine of a mammal during a period of about 40–80 min. starting about 1–3 h after the entry of the composition into the small intestine of said mammal.

13. The method of claim 12 wherein said sustained release pharmaceutical composition is administered to a human before normal bedtime in view of releasing said glucocorticoid into the small intestine at about 02:00–03:00 am.

14. The composition of claim 1 wherein said composition is in the form of a tablet.

15. The composition of claim 5 wherein said composition is in the form of a tablet.

16. The composition of claim 8 wherein said composition is in the form of a tablet.

17. The sustained release pharmaceutical composition for peroral treatment of rheumatoid arthritis as defined in claim 10, consisting essentially of:

2.5–7 mg of a glucocorticoid, and means for releasing at least 80% by weight of the glucocorticoid into the small intestine of a mammal during a period of about 40–80 min. starting about 1–3 h after the entry of the composition into the small intestine of said mammal, and one or more compounds selected from the group consisting of PVP, glidants and diluents.

18. The sustained release pharmaceutical composition for peroral treatment of rheumatoid arthritis as defined in claim 14, consisting essentially of:

2.5–7 mg of a glucocorticoid, said glucocorticoid being in a form such that at least 80% by weight of the glucocorticoid is released into the small intestine of a mammal during a period of about 40–80 min. starting about 1–3 h after the entry of the composition into the small intestine of said mammal, and one or more compounds selected from the group consisting of PVP, glidants and diluents.

\* \* \* \* \*